United States Patent [19]

Brickl et al.

[11] 4,225,619
[45] Sep. 30, 1980

[54] SUBSTITUTED FLUORACYLRESORCINOLS

[75] Inventors: Rolf Brickl; Hans Eberhardt; Karl-Richard Appel, all of Biberach; Uwe Lechner, Ummendorf; Walter Merk, Biberach, all of Fed. Rep. of Germany

[73] Assignee: Boehringer Ingelheim GmBH, Ingelheim am Rhein, Fed. Rep. of Germany

[21] Appl. No.: 21,777

[22] Filed: Mar. 19, 1979

Related U.S. Application Data

[63] Continuation of Ser. No. 786,265, Apr. 11, 1977, abandoned.

[30] Foreign Application Priority Data

Apr. 14, 1976 [DE] Fed. Rep. of Germany ....... 2616479

[51] Int. Cl.³ .................. A01N 35/04; C07C 49/82
[52] U.S. Cl. ...................................... 424/331; 568/31; 260/410.5; 568/43; 560/254; 560/255; 560/108; 560/109; 560/71; 260/465 D; 260/465 F; 424/308; 424/311; 424/312; 424/304; 568/306; 568/329; 568/330; 568/331; 568/337
[58] Field of Search ...................... 260/592; 424/331; 71/122, 123

[56] References Cited

U.S. PATENT DOCUMENTS

| | | | |
|---|---|---|---|
| 3,184,379 | 5/1965 | Lukes et al. | 424/331 |
| 3,205,058 | 9/1965 | Leasure | 71/123 |
| 3,931,329 | 1/1976 | Endres et al. | 260/592 |
| 3,933,472 | 1/1976 | Buckman et al. | 71/123 |

Primary Examiner—Natalie Trousof
Assistant Examiner—James H. Reamer
Attorney, Agent, or Firm—Hammond & Littell, Weissenberger & Muserlian

[57] ABSTRACT

Compounds of the formula

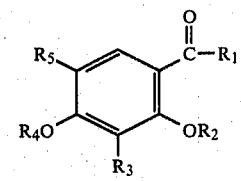

wherein
$R_1$ is perfluoroalkyl of 1 to 8 carbon atoms or 2,2,3,3-tetrafluoro-cyclobutyl,
$R_2$ and $R_4$, which may be identical to or different from each other, are each hydrogen, alkyl of 1 to 10 carbon atoms, aliphatic acyl of 2 to 18 carbon atoms, benzoyl, salicyloyl or phenylacetyl, and
$R_3$ and $R_5$, which may be identical to or different from each other, are each alkyl of 3 to 18 carbon atoms, halogen, nitro, p-toluenesulfonyl, cyclopentyl, cyclohexyl, cycloheptyl, cyclododecyl, methylcyclohexyl, dimethylcyclohexyl, benzyl, methylthio or

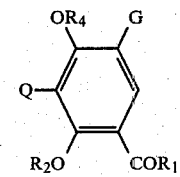

where
$R_1$, $R_2$ and $R_4$ have the meanings previously defined,
Q is —CH₂— or —S—, and
G is $R_5$, as above defined, or
Q is $R_3$, as above defined, and
G is —CH₂— or —S—,
$R_3$ may, in addition, also be hydroxyl, methoxy, methyl or cyano, and
$R_5$ may also be methyl, or
one of substituents $R_3$ and $R_5$ is hydrogen or ethyl when the other has the meanings defined above except hydrogen, or when $R_1$ has the meanings defined above except trifluoromethyl, or when $R_2$ and $R_4$ have the meanings defined above except hydrogen or methyl. The compounds are useful as active ingredients in pharmaceutical, cosmetic and pesticidal compositions.

16 Claims, No Drawings

SUBSTITUTED FLUORACYLRESORCINOLS

This is a continuation, of Ser. No. 786,265, filed Apr. 11, 1977 now abandoned.

This invention relates to novel substituted fluoracylresorcinols, as well as to various methods of preparing these compounds.

More particularly, the present invention relates to a novel class of substituted fluoracylresorcinols represented by the formula

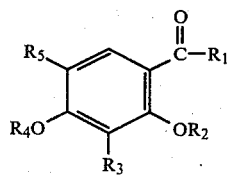

wherein $R_1$ is perfluoroalkyl of 1 to 8 carbon atoms or 2,2,3,3-tetrafluoro-cyclobutyl, $R_2$ and $R_4$, which may be identical to or different from each other, are each hydrogen, alkyl of 1 to 10 carbon atoms, aliphatic acyl of 2 to 18 carbon atoms, benzoyl, salicyloyl or phenylacetyl, and $R_3$ and $R_5$, which may be identical to or didferent from each other, are each alkyl of 3 to 18 carbon atoms, halogen, nitro, p-toluenesulfonyl, cyclopentyl, cyclohexyl, cycloheptyl, cyclododecyl, methylcyclohexyl, dimethylcyclohexyl, benzyl, methylthio or

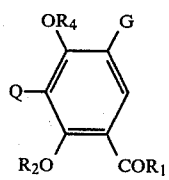

where $R_1$, $R_2$ and $R_4$ have the meanings previously defined,

Q is —$CH_2$— or —S—, and

G is $R_5$, as above defined, or

Q is $R_3$, as above defined, and

G is —$CH_2$— or —S—, $R_3$ may, in addition, also be hydroxyl, methoxy, methyl or cyano, and $R_5$ may also be methyl, or one of substituents $R_3$ and $R_5$ is hydrogen or ethyl when the other has the meanings defined above except hydrogen, or when $R_1$ has the meanings defined above except trifluoromethyl, or when $R_2$ and $R_4$ have the meanings defined above except hydrogen or methyl.

The compounds embraced by formula I may be prepared by the following methods:

Method A

By acylation of a resorcinol compound of the formula

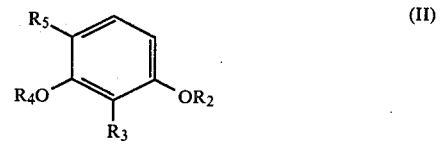

wherein $R_2$ to $R_5$ have the meanings hereinbefore defined, with a carboxylic acid or a reactive derivative thereof of the formula $$R_1\text{—COY} \quad (III)$$

wherein $R_1$ has the defined meanings and Y is hydroxyl, amino, acyloxy, alkoxy or halogen, in the presence of a Friedel-Crafts catalyst and of a solvent at temperatures between —80° C. and the boiling point of the solvent, preferably, however, at room temperature.

Suitable solvents include aliphatic hydrocarbons, carbon disulfide, halogenated, especially chlorinated aliphatic hydrocarbons, ethers, aromatic hydrocarbons such as benzene, toluene, chlorobenzene or dichlorobenzene, but also inorganic solvents such as phosphorus oxychloride, polyphosphoric acid, phosphoric acid or sulfuric acid.

Suitable catalysts are Lewis-acids such as anhydrous aluminum chloride, iron(III)chloride, zinc chloride, boron trifluoride or the etherates thereof, tin(IV)chloride, antimony-tri- or penta-halides, phosphorus-tri- or penta-halides, phosphorus pentoxide or inorganic acids such as hydrochloric acid, hydrofluoric acid, sulfuric acid, polyphosphoric acid or chlorosulfonic acid, or strong organic acids such as p-toluenesulfonic acid.

Method B

By reaction of a resorcinol compound of the formula

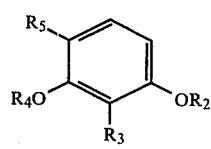

wherein $R_2$ to $R_5$ have the meanings previously defined, under the conditions of the ketone synthesis according to Hösch with a perfluorocarboxylic acid nitrile of the formula $$R_1\text{—CN} \quad (IV)$$

wherein $R_1$ has the meanings defined above.

The reaction is carried out at temperatures between —80° C. and the boiling point of the solvent in the presence of Lewis-acids as catalysts and an organic solvent, preferably at —20° to +80° C.

Suitable Lewis-acdis are, for example, anhydrous aluminum chloride, zinc chloride especially in the presence of hydrochloric acid, further iron(III)chloride and tin(IV)chloride, titanium tetrachloride, chromium trichloride, boron trifluoride, p-toluenesulfonic acid, phosphoric acid, polyphosphoric acid or hydrofluoric acid. Suitable solvents, for example, are ethers, chlorobenzene, nitrobenzene, xylene and phosphorus oxychloride.

Method C

For the preparation of a compound of the formula I wherein $R_2$ and/or $R_4$ are hydrogen, by rearrangement of a perfluoroacylresorcinol of the formula

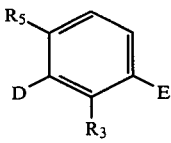
(V)

wherein $R_3$ and $R_5$ are as hereinabove defined and D is —$OR_4$ when E is —O—$COR_1$, or D is —O—$COR_1$ when E is —$OR_2$, or both D and E are —O—$COR_1$, where $R_1$, $R_2$ and $R_4$ have the meanings hereinbefore defined.

The reaction is preferably carried out in the presence of a Lewis-acid as catalyst, optionally in the presence of a solvent, at temperatures between 0° and 150° C.

Suitable Lewis-acids are, for example, anhydrous zinc chloride, anhydrous aluminum chloride, zinc chloride in the presence of a hydrohalic acid, as well as iron(III)chloride and tin(IV)chloride. Suitable solvents are, for example, ethers or aromatic hydrocarbons, such as chlorobenzene, nitrobenzene, toluene, dichlorobenzene or xylene, and phosphorus oxychloride.

Method D

For the preparation of a compound of the formula I wherein $R_3$ and/or $R_5$ are halogen, nitro or p-toluenesulfonyl, by reaction of a perfluoroacylresorcinol of the formula

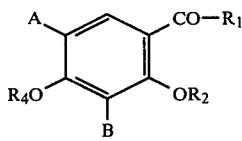
(VI)

wherein $R_1$, $R_2$ and $R_4$ have the meanings hereinbefore defined, and one of A and B is hydrogen, while the other already has the meanings of $R_3$ or $R_5$, with a compound of the formula $R_7Z$ (VII)

wherein $R_7$ is halogen, nitro or sulfonyl, and Z is halogen or hydroxyl. The reaction is carried out in a suitable solvent at temperatures between −20° and 150° C. Suitable solvents for the reaction with halogens ($R_7$ and Z are both halogen) are especially ethers, such as diethyl ether or dioxane, or glacial acetic acid. For the reaction with nitric acid and sulfuric acid, the acids or mixtures thereof may simultaneously serve as solvents.

Method E

For the preparation of a compound of the formula I, wherein $R_3$ and/or $R_5$ are alkyl of 3 to 18 carbon atoms, by reaction of a perfluoroacylresorcinol of the formula VI, with an unsaturated aliphatic hydrocarbon or a secondary alcohol of 3 to 18 carbon atoms. This alkylation is either carried out in the presence of an acid, such as phosphoric acid, polyphosphoric acid, sulfuric acid, glacial acetic acid or phosphorus oxychloride, or of a Lewis-acid, such as anhydrous aluminum chloride, iron(III)chloride, tin(IV)chloride, phosphorus pentoxide, zinc chloride or phosphorus pentachloride, in a solvent, such as ether, chlorobenzene, nitrobenzene or phosphorus oxychloride, at temperatures between 30° and 150° C.

Method F

For the preparation of a compound of the formula I, wherein $R_3$ is

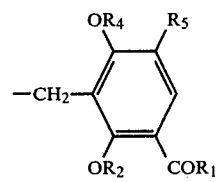

and $R_5$ has the meanings hereinbefore defined, or $R_5$ is

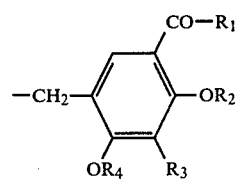

and $R_3$ has the above defined meanings, by condensation of 2 mols of a compound of the formula

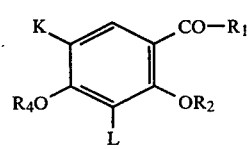
(VIa)

wherein either K is $R_5$ and L is hydrogen, or L is $R_3$ and K is hydrogen and $R_1$, $R_2$ and $R_4$ are as hereinbefore defined, with one mol of formaldehyde. The condensation takes place upon addition of the acid after standing for a while at room temperature, or by heating a solution of the reaction partners, optionally in an inert solvent, at temperatures up to the boiling point of the solvent.

The compounds of the formula I, wherein $R_2$ and/or $R_4$ are hydrogen, obtained by the above methods may, if desired, be subsequently converted into compounds of the formula I, wherein $R_2$ and/or $R_4$ have the remaining meanings stated above, by means of etherification, for instance with an alkyl halide, or by esterification, for instance with an acid halide or an acid anhydride.

The starting compounds of the formula I are either known from the literature or may be prepared according to processes known from the literature, for example by acylation of a known compound of the formula

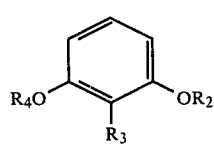
(VIII)

with a compound of the formula $R_5'$—COY (IX)

wherein Y has the meanings hereinbefore defined and R₅' is an optionally substituted alkyl group as defined for R₅, but which is shortened by a —CH₂-group. The formed acyl compound is subsequently catalytically reduced with hydrogen to the corresponding compound of the formula II which is alkylated in the 5-position.

On the other hand, the starting compounds of the formula II wherein R₅ is halogen, may be obtained by halogenating a compound of the formula VIII.

The compounds of the formulas II and VIII may, when R₃ is alkyl, also be obtained from a known compound of the formula

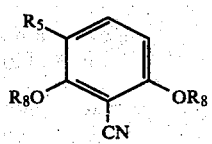  (X)

wherein R₅ has the meanings hereinbefore defined and R₈ is alkyl, by reaction with an aliphaic Grignard-compound of the formula R₃'-MgHal (R₃' is alkyl shortened by a —CH₂-group comared with the alkyl group represented by R₃). Subsequently, the corresponding compound possessing an aliphatic acyl group in the 3-position is liberated by means of hydrolysis, the groups R₈ are optionally split off with anhydrous aluminum chloride, and the aliphatic acyl group is reduced to R₃ having the meaning of an alkyl group. If a compound of the formula II, wherein R₂ and R₄ are hydrogen are wanted, the correspondingly substituted 4-methyl-7-hydroxy-cumarin of the formula

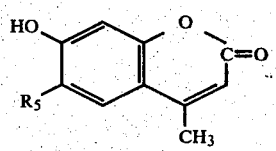  (XI)

wherein R₅ has the meanings hereinbefore defined, are esterified with a carboxylic acid or its derivative of the formula R₃'—COX, wherein R₃' and X have the above defined meanings, into a compound of the formula

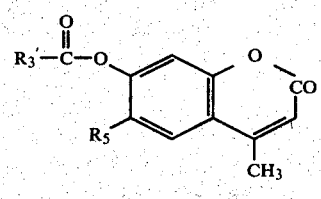  (XII)

which is subsequently rearranged into the corresponding compound of the formula

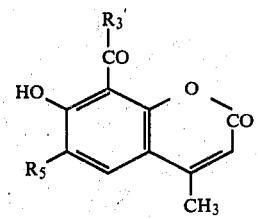  (XIII)

by means of anhydrous aluminum chloride, whereby a ketone of the formula

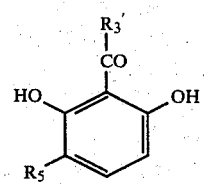  (XIV)

is formed by heating with sodium hydroxide solution and subsequent hydrolysis with sulfuric acid, which is catalytically reduced to a compound of the formula II (cf. Organic Synthesis Coll. Vol. 3, 281 ff), for example, with amalgamated zinc and hydrochloric acid. The compound thus obtained may, if desired, be subsequently converted into the corresponding compound of the formula II, wherein R₂ and R₄ are other tha hydrogen, for example by etherification or esterification.

The starting compounds of the formula V, wherein D or E is —O—COR₁, are obtained according to known methods by esterification of the corresponding compounds wherein D or E is hydroxyl.

The following examples illustrate the present invention and will enable others skilled in the art to understand it more completely. It should be understood, however, that the invention is not limited solely to examples given below.

EXAMPLE 1

2,4-Dihydroxy-5-n-hexyl-trifluoroacetophenone by method A 194 gm (1 mol) of 4-n-hexyl-resorcinol were suspended in 3 liters of ethylene chloride. While stirring the suspension at about 20° C., a total of 300 gm (2 mols) of aluminum chloride were added in several portions, and then 260 gm (1.2 mols) of trifluoroacetic acid anhydride were added dropwise over a period of about 1½ hours to the mixture at 15°-20° C.; the latter temperature range was maintained by cooling the reaction mixture on an ice water bath. Thereafter, the reaction mixture was stirred for three hours more, and was then allowed to stand for one to two days at room temperature. Subsequently, the reaction mixture was poured over about 2.5 kg of ice while stirring and exterior cooling, taking care that the temperature of the aqueous mixture did not rise above 25° C. The organic phase was separated, and the aqueous phase was washed three times with 500 ml each of ethylene chloride. The organic solutions were combined, washed with 1 liter of water, dried over calcium chloride, and evaporated. The residue was recrystallized from heptane, yielding 246 gm (85% of theory) of the compound of the formula

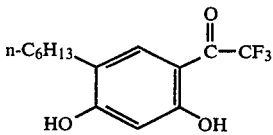

which had a melting point of 90° C.

Using an analogous procedure, the following compounds were also prepared:

(a) 2,4-Dihydroxy-3-methyl-trifluoroacetophenone from 2-methyl-resorcinol in ethylene chloride; m.p. 101° C., yield: 90% of theory.

(b) 2,4-Dihydroxy-5-n-propyl-trifluoroacetophenone from 4-n-propyl-resorcinol in ethylene chloride; m.p. 95° C., yield: 87% of theory.

(c) 2,4-Dihydroxy-5-isopropyl-trifluoroacetophenone from 4-isopropyl-resorcinol in chloroform; m.p. 97° C., yield: 70% of theory.

(d) 2,4-Dihydroxy-3-n-propyl-trifluoroacetophenone from 2-n-propyl-resorcinol in ethylene chloride; m.p. 114° C., yield: 88% of theory.

(e) 2,4-Dihydroxy-3-isopropyl-trifluoroacetophenone from 2-isopropyl-resorcinol in ethylene chloride; m.p. 145° C., yield: 85% of theory.

(f) 2,4-Dihydroxy-5-n-butyl-trifluoroacetophenone from 4-n-butyl-resorcinol in ethylene chloride; m.p. 96° C., yield: 82% of theory.

(g) 2,4-Dihydroxy-5-isobutyl-trifluoroacetophenone from 4-isobutyl-resorcinol in ethylene chloride; m.p. 90° C., yield: 84% of theory.

(h) 2,4-Dihydroxy-3-isobutyl-trifluoroacetophenone from 2-isobutyl-resorcinol in ethylene chloride; m.p. 114° C., yield: 78% of theory.

(i) 2,4-Dihydroxy-5-tert.butyl-trifluoroacetophenone from 4-tert.butyl-resorcinol in ethylene chloride; m.p. 159° C., yield: 80% of theory.

(j) 2,4-Dihydroxy-5-(2'-methyl-n-propyl)-trifluoroacetophenone of the formula

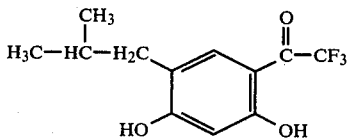

from 4-(2'-methyl-n-propyl)-resorcinol in ethylene chloride; m.p. 90° C., yield: 78% of theory.

(k) 2,4-Dihydroxy-5-n-pentyl-trifluoroacetophenone from 4-n-pentyl-resorcinol in ethylene chloride; m.p. 97° C., yield: 86% of theory.

(l) 2,4-Dihydroxy-5-cyclopentyl-trifluoroacetophenone from 4-cyclopentyl-resorcinol in ethylene chloride; m.p. 94° C., yield: 75% of theory;

(m) 2,4-Dihydroxy-3-isopentyl-trifluoroacetophenone from 2-isopentyl-resorcinol in ethylene chloride; m.p. 101° C., yield: 84% of theory.

(n) 2,4-Dihydroxy-3-n-pentyl-trifluoroacetophenone from 2-n-pentyl-resorcinol in ethylene chloride; m.p. 105° C., yield: 87% of theory.

(o) 2,4-Dihydroxy-5-cyclohexyl-trifluoroacetophenone from 4-cyclohexyl-resorcinol in ethylene chloride; m.p. 80° C., yield: 78% of theory.

(p) 2,4-Dihydroxy-5-n-heptyl-trifluoroacetophenone from 4-n-heptyl-resorcinol in ethylene chloride; m.p. 85° C., yield: 79% of theory;

(q) 2,4-Dihydroxy-5-benzyl-trifluoroacetophenone from 4-benzyl-resorcinol in ethylene chloride; m.p. 114° C., yield: 80% of theory.

(r) 2,4-Dihydroxy-3-(4'-methyl-cyclohexyl)-trifluoroacetophenone from 2-(4'-methyl-cyclohexyl)-resorcinol in ethylene chloride; m.p. 143° C., yield: 76% of theory.

(s) 2,4-Dihydroxy-5-(3',5'-dimethyl-cyclohexyl)-trifluoroacetophenone from 4-(3',5'-dimethyl-cyclohexyl)-resorcinol in ethylene chloride; m.p. 126° C., yield: 79% of theory.

(t) 2,4-Dihydroxy-5-n-nonyl-trifluoroacetophenone from 4-n-nonyl-resorcinol in ethylene chloride; m.p. 87° C., yield: 85% of theory.

(u) 2,4-Dihydroxy-5-n-dodecyl-trifluoroacetophenone from 4-n-dodecyl-resorcinol in ethylene chloride; m.p. 92° C., yield: 84% of theory.

(v) 2,4-Dihydroxy-5-chloro-trifluoroacetophenone from 4-chloro-resorcinol in ethylene chloride; m.p. 110° C., yield: 90% of theory.

(w) 2,4-Dihydroxy-5-bromo-trifluoroacetophenone from 4-bromo-resorcinol in ethylene chloride; m.p. 81° C., yield: 88% of theory.

(x) 2,3,4-Trihydroxy-trifluoroacetophenone from pyrogallol; m.p. 134° C., yield: 75% of theory (y) 2,4-Dihydroxy-3-methoxy-trifluoroacetophenone from 2-methoxy-resorcinol in ethylene chloride; m.p. 79° C., yield: 78% of theory.

(z) 2,4-Dihydroxy-5-(2',2',3',3'-tetrafluoro-cyclobutylmethyl)-trifluoroacetophenone of the formula

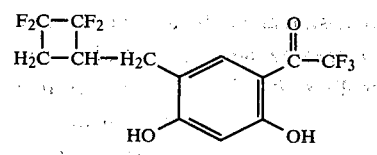

from 4-(2',2',3',3'-tetrafluoro-cyclobutyl-methyl)-resorcinol in ethylene chloride; m.p. 122° C., yield: 76% of theory.

(aa) 2,4-Dihydroxy-5-methylthio-trifluoroacetophenone from 4-methylthio-resorcinol in ethylene chloride; m.p. 57° C., yield: 68% of theory.

(bb) 2,3,4-Trihydroxy-5-cyclohexyl-trifluoroacetophenone from 4-cyclohexyl-pyrogallol in ethylene chloride; m.p. 128° C., yield: 78% of theory.

(cc) 2,3,4-Trihydroxy-5-ethyl-trifluoroacetophenone from 4-ethyl-pyrogallol in ethylene chloride; m.p. 82° C., yield: 80% of theory.

(dd) 2,4-Dihydroxy-3-chloro-trifluoroacetophenone from 2-chloro-resorcinol in ethylene chloride; m.p. 113° C., yield: 83% of theory.

(ee) 2,4-Dihydroxy-5-n-octyl-trifluoroacetophenone from 4-n-octyl-resorcinol in ethylene chloride; m.p. 87° C., yield: 74% of theory.

(ff) 2,4-Dihydroxy-3-cyano-trifluoroacetophenone of the formula

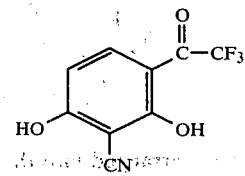

from 2,6-dihydroxy-benzonitrile in ethylene chloride; m.p. 210° C., yield: 62% of theory.

(gg) 2,2',4,4'-Tetrahydroxy-5,5'-trifluoroacetyl-diphenylsulfide of the formula

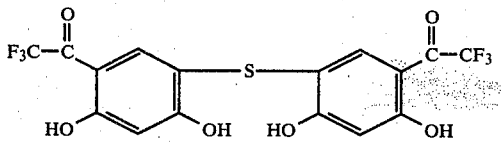

from 2,2',4,4'-tetrahydroxy-diphenylsulfide in ethylene chloride; m.p. 172° C., yield: 10% of theory.

(hh) 2,2',4,4'-Tetrahydroxy-5-trifluoroacetyl-diphenylsulfide of the formula

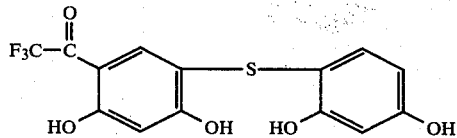

from 2,2',4,4'-tetrahydroxy-diphenylsulfide in ethylene chloride; m.p. 204° C., yield: 20% of theory.

EXAMPLE 2

2,4-Dihydroxy-5-n-hexyl-perfluoropropiophenone by method A

In analogy to Example 1, 1.94 gm of n-hexyl-resorcinol were admixed with 30 ml of ethylene chloride and 3 gm of aluminum chloride, and then 3.6 gm of perfluoropropionic acid anhydride were added dropwise to the mixture. The reaction mixture was subsequently stirred for 1 to 2 days at room temperature, and was finally worked up as described in Example 1. 72% of theory of the compound of the formula

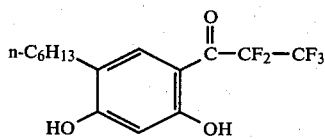

having a melting point of 62° C. were obtained.

In analogous manner, the following compounds were also prepared:

(a) 2,4-Dihydroxy-perfluoropropiophenone from resorcinol; m.p. 80° C., yield: 72% of theory.

(b) 2,4-Dihydroxy-3-methyl-perfluoropropiophenone from 2-methyl-resorcinol; m.p. 69° C., yield: 76% of theory.

(c) 2,4-Dihydroxy-5-methyl-perfluoropropiophenone from 4-methyl-resorcinol; m.p. 140° C., yield: 75% of theory.

(d) 2,3,4-Trihydroxy-perfluoropropiophenone from pyrogallol; m.p. 105° C., yield: 60% of theory.

EXAMPLE 3

Using a procedure analogous to that described in Example 2, the following compounds were prepared from perfluorobutyric acid anhydride and the indicated resorcinol compound:

(a) 2,4-Dihydroxy-perfluorobutyrophenone from resorcinol; m.p. 90° C., yield: 66% of theory.

(b) 2,4-Dihydroxy-3-methyl-perfluorobutyrophenone from 2-methyl-resorcinol; m.p. 75° C., yield: 65% of theory.

(c) 2,4-Dihydroxy-5-n-hexyl-perfluorobutyrophenone from 4-n-hexyl-resorcinol; m.p. 57° C., yield: 60% of theory.

EXAMPLE 4

2,4-Dihydroxy-5-n-hexyl-perfluoropropiophenone by method A

A solution of 1.94 gm of 4-n-hexyl-resorcinol in 30 ml of ethylene chloride was admixed with a catalytic amount of boron trifluoride etherate and 2.2 gm of perfluoropropionic acid, and the mixture was refluxed for 5 hours. Thereafter, the reaction mixture was worked up as described in Example 1, yielding 1.4 gm (41% of theory) of 2,4-dihydroxy-5-n-hexyl-perfluoropropiophenone, m.p. 62° C.

In analogous manner 2,4-dihydroxy-3-methyl-perfluorocaprylophenone, $R_f$-value=0.87 (eluant: petroleum ether/chloroform/ethyl acetate=3/6/1) was prepared.

EXAMPLE 5

2,4-Dihydroxy-3-methyl-5-chloro-trifluoroacetophenone by method D 150 ml of sulfuryl chloride were added to a solution of 220 gm of 2,4-dihydroxy-3-methyl-trifluoroacetophenone in 3 liters of ethylene chloride, and the mixture was stirred for three hours. Thereafter, while cooling, 300 ml of water were added to the reaction mixture of decompose the excess, unreacted sulfuryl chloride. After separation of the aqueous phase, the organic phase was washed three times with 150 ml each of water, then dried with sodium sulfate, and evaporated to about 20% of its original volume. 150 gm of practically pure 2,4-dihydroxy-3-methyl-5-chloro-trifluoroacetophenone precipitated out. After complete evaporation of the mother liquor, the residue was recrystallized from a mixture of methylene chloride and heptane (1:1), yielding an additional 46 gm of the reaction product. Total yield: 196 gm (76% of theory) of the compound of the formula

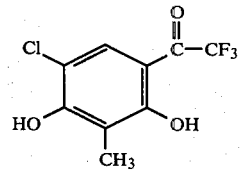

having a melting point of 96° C.

In analogous manner, but in the absence of a solvent, the following compounds were also prepared with sulfuryl chloride:

(a) 2,4-Dihydroxy-3,5-dichloro-trifluoroacetophenone from 2,4-dihydroxy-trifluoroacetophenone; m.p. 101° C.

(b) 2,4-Dihydroxy-3-chloro-5-n-hexyl-trifluoroacetophenone from 2,4-dihydroxy-5-n-hexyl-trifluoroacetophenone; m.p. 40° C.

EXAMPLE 6

2,4-Dihydroxy-3-chloro-trifluoroacetophenone by method D 3 mg (0.015 mol) of 2,4-dihydroxy-trifluoroacetophenone were dissolved in 25 ml of carbon tetrachloride, and a solution of 2.2 gm (0.02 mol) of tert.butyl hypochlorite in 100 ml of carbon tetrachloride was added. After standing for 1 hour, the solution was evaporated, and the residue was recrystallized from n-hexane, yielding 90% of theory of the compound of the formula

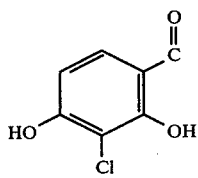

which had a melting point of 110° C.

The following compounds were prepared in analogous manner with tert.butyl hypochlorite:

(a) 2,4-Dihydroxy-3-chloro-5-isopropyl-trifluoroacetophenone m.p. 35° C., from 2,4-dihydroxy-5-isopropyl-trifluoroacetophenone.

(b) 2,4-Dihydroxy-3-chloro-5-tert.butyl-trifluoroacetophenone m.p. 40° C., from 2,4-dihydroxy-5-tert.tubyl-trifluoroacetophenone.

(c) 2,4-Dihydroxy-3-isopropyl-5-chloro-trifluoroacetophenone m.p. 42° C. from 2,4-dihydroxy-3-isopropyl-trifluoroacetophenone.

(d) 2,4-Dihydroxy-3-methyl-5-chloro-trifluoroacetophenone m.p. 96° C., from 2,4-dihydroxy-3-methyl-trifluoroacetophenone.

EXAMPLE 7

2,4-Dihydroxy-3,5-dibromo-trifluoroacetophenone by method D 2 ml of bromine were added dropwise to a solution of 4 gm of 2,4-dihydroxy-trifluoroacetophenone in 5 ml of glacial acetic acid. After 1 to 2 days of standing, a substance crystallized out which was collected by suction filtration and recrystallized from hexane/heptane (1:1), yielding 3.6 gm (49% of theory) of 2,4-dihydroxy-3,5-dibromo-trifluoroacetophenone, m.p. 81° C.

The following compound was prepared in analogous manner:

(a) 2,4-Dihydroxy-3-bromo-5-n-hexyl-trifluoroacetophenone from 2,4-dihydroxy-5-n-hexyl-trifluoroacetophenone; m.p. 39° C., yield: 43% of theory.

EXAMPLE 8

2,4-Dihydroxy-5-p-toluenesulfonyl-trifluoroacetophenone

A mixture consisting of 5 gm of 2,4-dihydroxy-trifluoroacetophenone, 10 gm of p-toluenesulfonic acid chloride, 10 gm of iron(III)chloride (anhydrous) and 10 ml of phosphorus oxychloride was heated at 120° C. for 10 hours. Subsequently, 100 ml of water were added, and the mixture was suctionfiltered. The filtercake was subjected to steam distillation to remove unreacted p-toluenesulfonic acid and then recrystallized from petroleum ether, yielding 3.6 gm (40% of theory) of the compound of the formula

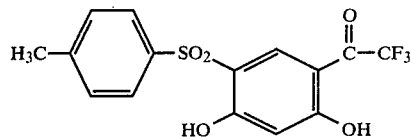

which had a melting point of 145° C.

EXAMPLE 9

Using a procedure analogous to that described in Example 8, but substituting aluminum chloride for ferric chloride as the catalyst, 2 gm (22% of theory) of 2,4dihydroxy-3-p-toluenesulfonyl-trifluoroacetophenone, m.p. 127° C., were obtained from 2,4-dihydroxy-trifluoroacetophenone.

EXAMPLE 10

2,4-Dihydroxy-3-methyl-5-nitro-trifluoroacetophenone by method D 6 ml of 26% nitric acid were added dropwise to a solution of 4.5 gm of 2,4-dihydroxy-3-methyl-trifluoroacetophenone in 20 ml of glacial acetic acid, while cooling the mixture on an ice bath. After 20 hours of standing, the reaction mixture was poured into water, and the aqueous mixture was suction-filtered. The filter cake was recrystallized from heptane, yielding 1.1 gm (21% of theory) of the compound of the formula

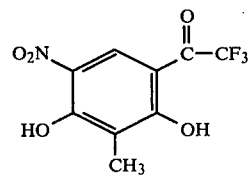

which had a melting point of 104° C.

Using an analogous procedure, the following compounds were also prepared:

(a) 2,4-Dihydroxy-5-nitro-trifluoroacetophenone m.p. 81° C., from 2,4-dihydroxy-trifluoroacetophenone.

(b) 2,4-Dihydroxy-3,5-dinitro-trifluoroacetophenone m.p. 68° C., from 2,4-dihydroxy-trifluoroacetophenone with a mixture of 65% nitric acid and concentrated sulfuric acid.

EXAMPLE 11

2,4-Dihydroxy-3-(1'-methyl-pentyl)-trifluoroacetophenone 10 gm of 2,4-dihydroxy-trifluoroacetophenone and 12.6 gm of 1-hexane were dissolved in 40 ml of phosphorus oxychloride and 5 gm of phosphorus pentoxide were added, while stirring. The mixture was heated at 50° C. for 6 hours, while vigorously stirring. The reaction mixture was then poured into ice water to decompose the phosphorus oxychloride, and the precipitated oil was isolated by extracting the reaction mixture 5 times with 100 ml each of n-hexane. In order to remove unreacted 2,4-dihydroxy-trifluoroacetophenone, the combined n-hexane extracts were washed 5 times with 80 ml each of aqueous 60% methanol, and then the solution was extracted 5 times with 100 ml each of aqueous 90% methanol. The methanol combined extracts were completely evaporated in a rotary evaporator, and the residue was recrystallized from n-pentane, yielding 1.5 gm (30% of theory) of the compound of the formula

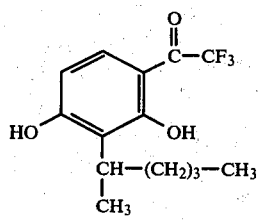

which had a melting point of 97° C.

In analogous manner, the following compounds were also prepared:

(a) 2,4-Dihydroxy-3-isobutyl-trifluoroacetophenone m.p. 114° C. from butene and 2,4-dihydroxy-trifluoroacetophenone.

(b) 2,4-Dihydroxy-3-cyclododecyl-trifluoroacetophenone m.p. 166° C. from cyclododecene and 2,4-dihydroxy-trifluoroacetophenone.

(c) 2,4-Dihydroxy-3-isodecyl-trifluoroacetophenone m.p. 98° C. from 1-decene and 2,4-dihydroxy-trifluoroacetophenone.

(d) 2,4-Dihydroxy-3-cyclopentyl-trifluoroacetophenone m.p. 166° C. from cyclopentene and 2,4-dihydroxy-trifluoroacetophenone.

(e) 2,4-Dihydroxy-3-cycloheptyl-trifluoroacetophenone m.p. 174° C. from cycloheptene and 2,4-dihydroxy-trifluoroacetophenone.

(f) 2,4-Dihydroxy-3-isopropyl-trifluoroacetophenone m.p. 145° C. from propene and 2,4-dihydroxy-trifluoroacetophenone.

(g) 2,4-Dihydroxy-3-isododecyl-trifluoroacetophenone m.p. 96° C. from 1-dodecene and 2,4-dihydroxy-trifluoroacetophenone.

(h) 2,4-Dihydroxy-3-isooctadecyl-trifluoroacetophenone m.p. 98° C. from 1-octadecene and 2,4-dihydroxy-trifluoroacetophenone.

EXAMPLE 12

2,4-Dihydroxy-3-hexyl-trifluoroacetophenone by method E 10 gm of 2,4-dihydroxy-trifluoroacetophenone and 12.6 gm of 1-hexene were dissolved in a mixture of 30 ml of concentrated sulfuric acid and 30 ml of glacial acetic acid, and the solution was heated at 60° C. for 5 hours. Subsequently, the reaction mixture was poured into ice water and the precipitated oil was isolated by extracting the aqueous mixture 5 times with 100 ml each of n-hexane. To remove unreacted 2,4-dihydroxy-trifluoroacetophenone, the n-hexane solution was washed 5 times with 80 ml each of aqueous 60% methanol, then the solution was extracted 5 times with 100 ml each of aqueous 90% methanol. The combined methanol extracts were evaporated in a rotary evaporator, and the residue was recrystallized from n-pentane, yielding 2 gm (40% of theory) of 2,4-dihydroxy-3-hexyl-trifluoroacetophenone, m.p. 97° C.

EXAMPLE 13

2,4-Dihydroxy-3-methyl-trifluoroacetophenone monoacetate 4.4 gm (0.02 mol) of 2,4-dihydroxy-3-methyl-trifluoroacetophenone were dissolved in 25 ml of benzene, and 3.2 gm (0.04 mol) of acetyl chloride and 3.6 gm (0.045 mol) of pyridine were added to the solution while stirring. After stirring at room temperature for 2 hours, the mixture was poured into water, and the benzene solution was separated. This solution was washed with 50 ml of water and dried with sodium sulfate. After evaporation is a rotary evaporator, the residue was recrystallized from n-hexane, yielding 4.5 gm (86.5% of theory) of the monoacetate of 2,4-dihydroxy-3-methyl-trifluoroacetophenone, m.p. 49°-50° C.

The following compounds were prepared in analogous manner:

(a) 2,4-Dihydroxy-5-chloro-trifluoroacetophenone monoacetate from 2,4-dihydroxy-5-chloro-trifluoroacetophenone and acetyl chloride; m.p. 80°-83° C., yield: 71.5% of theory.

(b) 2,4-Dihydroxy-5-chloro-trifluoroacetophenone monostearate from 2,4-dihydroxy-5-chloro-trifluoroacetophenone and stearoyl chloride; m.p. 51° C., yield: 40% of theory.

(c) 2,4-Dihydroxy-3-methyl-trifluoroacetophenone monoundecylenate from 2,4-dihydroxy-3-methyl-trifluoroacetophenone and 11-undecylenic acid chloride. This compound is purified by distillation. B.p.=165° C. at 0.07 mm Hg, yield: 65% of theory.

(d) 2,4-Dihydroxy-5-chloro-trifluoroacetophenone monoundecylenate from 2,4-dihydroxy-5-chloro-trifluoroacetophenone and 11-undecylenic acid chloride. This compound was purified by distillation. B.p.=168° C. at 0.07 mm Hg, yield: 65% of theory.

(e) 2,4-Dihydroxy-5-n-hexyl-trifluoroacetophenone monoacetate from 2,4-dihydroxy-5-n-hexyl-trifluoroacetophenone and acetyl chloride, m.p. 30° C., yield: 83% of theory.

(f) 2,4-Dihydroxy-5-n-hexyl-trifluoroacetophenone monostearate from 2,4-dihydroxy-5-n-hexyl-trifluoroacetophenone and stearoyl chloride; yield: 77% of theory.

(g) 2,4-Dihydroxy-3-methyl-trifluoroacetophenone di-phenylacetate from phenylacetyl chloride and 2,4-dihydroxy-3-methyl-trifluoroacetophenone; m.p. 65° C., yield: 90% of theory.

EXAMPLE 14

Mixture of mono- and disalicylates of 2,4-dihydroxy-3-methyl-trifluoroacetophenone 32 gm of sodium salicylate and 2.2 gm of 2,4-dihydroxy-3-methyl-trifluoroacetophenone were dissolved in 20 ml of benzene, 3.2 gm of phosphorus oxychloride were added, and the mixture was refluxed for 2 hours. For decomposition of the phosphorus oxychloride the mixture was poured over 150 gm of ice, the benzene solution was separated, and the aqueous phase was extracted with 50 ml of benzene. The combined benzene solutions were washed with 100 ml of water, dried with sodium sulfate and evaporated, and the residue was recrystallized from 75% methanol. 40% of theory of a product having a melting point of 94°-98° C. was obtained which, according to UV-, IR- and NMR-spectra, was a mixture of mono- and disalicylate of 2,4-dihydroxy-3-methyl-trifluoroacetophenone.

EXAMPLE 15

2-Hydroxy-4-decyloxy-trifluoroacetophenone and 2,4-Didecyloxy-trifluoroacetophenone A mixture consisting of 10.3 gm (0.05 mol) of 2,4-dihydroxy-trifluoroacetophenone, 7 gm (0.05 mol) of potassium carbonate (dried), 26.8 gm (0.1 mol) of decyl iodide and 100 ml of acetone was refluxed for 5 hours.

The acetone was subsequently evaporated in a rotary evaporator, and 100 ml of water were added to the residue. The mixture was extracted with 100 ml of ethyl acetate, and the extract solution was dried with sodium sulfate. After evaporation in a rotary evaporator, the residual mixture of mono- and diether was fractionally distilled. In the first fraction at 0.1 mm Hg and 80° C. the unreacted decyl iodide was contained. The ethers were then recrystallized in methanol.

Monoether: B.p. 150° C. at 0.1 mm Hg, m.p. 27°–28° C., yield: 9.2 gm (53.2% of theory)

Diether: B.p. 200° C. at 0.1 mm Hg, m.p. 37°–38° C., yield: 5.6 gm (23.0% of theory)

The following compounds were prepared in analogous manner:

(a) 2-Hydroxy-4-butoxy-trifluoroacetophenone from 2,4-dihydroxy-trifluoroacetophenone and butyl iodide; m.p. 66° C., yield: 28.5% of theory.

(b) 2,4-Dimethoxy-5-n-hexyl-trifluoroacetophenone from 2,4-dihydroxy-5-n-hexyl-trifluoroacetophenone and methyl iodide; m.p. 52° C., yield: 30.5% of theory.

EXAMPLE 15

2,4-Dimethoxy-trifluoroacetophenone 3 gm (0.015 mol) of 2,4-dihydroxy-trifluoroacetophenone were dissolved in 75 ml of methylene chloride. 0.6 gm (0.002 mol) of tetrabutylammonium bromide, a solution of 2 gm (0.05 mol) of sodium hydroxide in 75 ml of water, as well as 5 gm (0.04 mol) of dimethyl sulfate were added. After stirring vigorously for 5 hours, the mixture was poured into 100 ml of water, the aqueous mixture was acidified with 15% hydrochloric acid, and the organic phase was separated and evaporated after drying with sodium sulfate. The residue was recrystallized from n-pentane, yielding 2 gm (57% of theory) of the compound of the formula

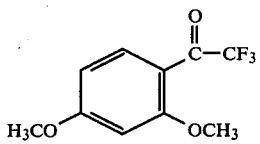

which had a melting point of 49° C.

EXAMPLE 16

Methylene-bis-(2,6-dihydroxy-3-trifluoroacetyl-5-ethyl-benzene by method F

A mixture consisting of 2.4 gm of 2,4-dihydroxy-5-ethyl-trifluoroacetophenone and 2 gm of paraformaldehyde was heated at 140° C. for 1 hour, and subsequently the mixture was recrystallized from heptane, yielding 2.3 gm (92% of theory) of the compound of the formula

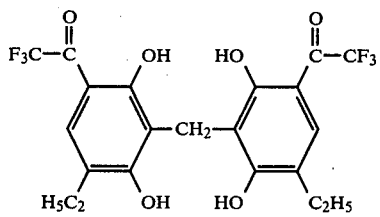

which had a melting point of 170° C.

The following compounds were prepared in analogous manner:

(a) Methylene-bis-(2,6-dihydroxy-3-trifluoroacetyl-5-methylbenzene) from 2,4-dihydroxy-5-methyl-trifluoroacetophenone; m.p. 234° C. yield: 92% of theory.

(b) Methylene-bis-(2,6-dihydroxy-3-trifluoroacetyl-5-n-propylbenzene) from 2,4-dihydroxy-5-n-propyl-trifluoroacetophenone; m.p. 153° C., yield: 90% of theory.

(c) Methylene-bis-(2,6-dihydroxy-3-trifluoroacetyl-5-n-butylbenzene) from 2,4-dihydroxy-5-n-butyl-trifluoroacetophenone; m.p. 145° C., yield: 91% of theory.

(d) Methylene-bis-(2,6-dihydroxy-3-trifluoroacetyl-5-n-pentylbenzene) from 2,4-dihydroxy-5-n-pentyl-trifluoroacetophenone; m.p. 131° C., yield: 90% of theory.

(e) Methylene-bis-(2,6-dihydroxy-3-trifluoroacetyl-5-n-hexylbenzene) from 2,4-dihydroxy-5-n-hexyl-trifluoroacetophenone; m.p. 120° C., yield: 93% of theory.

(f) Methylene-bis-(2,6-dihydroxy-3-trifluoroacetyl-5-n-dodecyl-benzene) from 2,4-dihydroxy-5-n-dodecyl-trifluoroacetophenone; m.p. 110° C., yield: 85% of theory.

(g) Methylene-bis-(2,6-dihydroxy-3-trifluoroacetyl-5-isopropyl-benzene) from 2,4-dihydroxy-5-isopropyl-trifluoroacetophenone; m.p. 140° C., yield: 89% of theory.

(h) Methylene-bis-(2,6-dihydroxy-3-trifluoroacetyl-5-benzyl-benzene) from 2,4-dihydroxy-5-benzyl-trifluoroacetophenone; m.p. 183° C., yield: 90% of theory.

(i) Methylene-bis-(2,6-dihydroxy-3-trifluoroacetyl-5-cyclohexyl-benzene) from 2,4-dihydroxy-5-cyclohexyl-trifluoroacetophenone; m.p. 206° C., yield: 85% of theory.

(j) Methylene-bis-(2,4-dihydroxy-3-isopropyl-5-trifluoroacetyl-benzene) from 2,4-dihydroxy-3-isopropyl-trifluoroacetophenone; m.p. 123° C., yield: 90% of theory.

EXAMPLE 17

Methylene-bis-(2,4-dihydroxy-3-methyl-5-trifluoroacetylbenzene) by method F 2.2 gm of 2,4-dihydroxy-3-methyl-trifluoroacetophenone were dissolved with 2 gm of paraformaldehyde in 10 ml of methanol. 7 ml of concentrated sulfuric acid were added to the solution, while stirring and cooling with ice, and the mixture was allowed to stand at room temperature for 5 hours. Then, water was added, the mixture was suction-filtered, and the filter cake was recrystallized from methanol/water (1:1), yielding 1.9 gm (87% of theory) of the compound of the formula

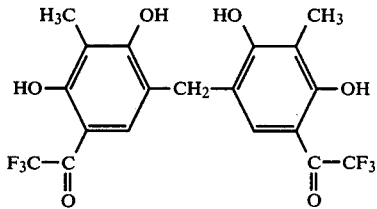

which had a melting point of 195° C.

The following compound was prepared in analogous manner:

Methylene-bis-(2,6-dihydroxy-3-trifluoroacetyl-5-chlorobenzene) from 2,5-dihydroxy-5-chloro-resorcinol, m.p. 205° C., yield: 87% of theory.

We have further discovered that the compounds of the formula I exhibit useful pharmacological and/or pesticidal properties. In particular, they are active against bacteria, dermatophytes, yeasts, molds and phytopathogenic fungi; they have an inhibitory effect on various key enzymes of carbohydrate metabolism and on cell cultures, and thus they delay accelerated processes of mitosis in and on the skin. Therefore, they are suitable for the treatment of acne, dandruff, bacterial skin infections, mycoses, psoriasis, ichthyosis, hyperkeratotic states of the skin, for combatting damping off diseases in plant cultures as well as for herbicidal use, e.g. against wild oats. Various compounds of the formula I also exhibit anthelmintic activity.

For example, the following known compounds were tested comparatively for their inhibitory effects on bacteria and fungi, cell cultures and enzyme activities:

| | |
|---|---|
| 2,4-Dihydroxy-trifluoroacetophenone | = A |
| 5-Ethyl-2,4-dihydroxy-trifluoroacetophenone | = B |
| 3-Ethyl-2,4-dihydroxy-trifluoroacetophenone | = C |
| 2,4-Dimethoxy-trifluoroacetophenone | = D |
| with the following compounds of this invention: | |
| 2,4-Dihydroxy-5-n-hexyl-trifluoroacetophenone | = E |
| 2,4-Dihydroxy-3-iso-butyl-trifluoroacetophenone | = F |
| 2,4-Dihydroxy-5-iso-pentyl-trifluoroacetophenone | = G |
| 2,4-Dihydroxy-3-(4'-methyl)-cyclohexyl-trifluoroacetophenone | = H |
| 2,4-Dihydroxy-5-(3',5'-dimethyl)-cyclohexyl-trifluoroacetophenone | = I |
| 2,4-Dihydroxy-5-n-nonyl-trifluoroacetophenone | = J |
| 2,4-Dihydroxy-3-iso-hexyl-trifluoroacetophenone | = K |
| 2,4-Dihydroxy-3-cyclododecyl-trifluoroacetophenone | = L |
| 2,4-Dihydroxy-3-isodecyl-trifluoroacetophenone | = M |
| 2,4-Dihydroxy-3-cyclopentyl-trifluoroacetophenone | = N |
| 2,4-Dihydroxy-3-cycloheptyl-trifluoroacetophenone | = O |
| 2,4-Dihydroxy-3-isopropyl-trifluoroacetophenone | = P |
| Methylene-bis-(2,6-dihydroxy-3-isopropyl-5-trifluoroacetyl)-benzene | = Q |
| Methylene-bis-(2,6-dihydroxy-3-ethyl-5-trifluoroacetyl)-benzene | = R |
| Methylene-bis-(2,4-dihydroxy-3-methyl-5-trifluoroacetyl)-benzene | = S |
| 2,4-Dihydroxy-3-methyl-trifluoroacetophenone | = T |
| 2,4-Dihydroxy-5-chloro-trifluoroacetophenone | = U |
| 2,4-Dihydroxy-3-methyl-pentafluoropropiophenone | = V |
| 2,4-Dihydroxy-5-n-decyl-trifluoroacetophenone | = W |
| 2,4-Dihydroxy-3-n-pentyl-trifluoroacetophenone | = X |
| 2,4-Dihydroxy-3-n-propyl-trifluoroacetophenone | = Y |
| Methylene-bis-(2,4-dihydroxy-3-isopropyl-5-trifluoroacetyl)-benzene | = Z |

The inhibitory effect on bacteria and fungi was examined by the serial dilution test and the agar diffusion test (hole-test). As bacteria were used: Staphylococcus aureus SG 511, Streptococcus Aronson, *Streptococcus pyogenes* At CC 86 68; as fungi: Candida albicans AT CC 10231, Trichophyton mentagrophytes AT CC 9129 and Aspergillus niger.
Serial dilution test:

Nutrient media

1. Meat extract broth: for St. aureus SG 511

| Recipe: | Peptone | 10 gm |
|---|---|---|
| | Meat extract | 8 gm |
| | Sodium chloride | 3 gm |
| | Sec. sodium phosphate (Na$_2$HPO$_4$) | 2 gm |
| | ad 1,000 ml of distilled water | (pH 7.2–7.4) |

Sterilization: 15 min. at 120° C. in the autoclave

2. Glucose broth: for Sc. Aronson and St. pyogenes
Recipe see meat extract broth. After sterilization 1 weight percent of glucose is added as a sterile 50% solution.

3. Sabouraud broth: for C. alb., Trich. mnt., A. niger

| Recipe: | Peptone from Casein | 10 gm |
|---|---|---|
| | Glucose | 40 gm |
| | Sodium chloride | 1 gm |
| | Sec. sodium phosphate (Na$_2$HPO$_4$) | 1 gm |

Sterilization: 5–10 min. at 120° C., a pH was not adjusted.

Standardization of the density of microorganisms

The age of the primary cultures is 24 hours for bacteria and 14 days for fungi. The standardization of the suspension of microorganisms is effected using a photometer according to Eppendorf (test tube $\phi$14 mm, filter 546 nm) and a suspension for comparison consisting of barium sulfate, this suspension being created by adition of 3.0 ml of 1% barium chloride solution to 97 ml of 1% sulfuric acid. After the standardization the bacteria were further diluted to a concentration of 1:1000 by means of sodium chloride solution, the fungi were used in an undiluted state.

Preparation of the substance concentration 40 mgm of the substance were put into a 10 ml measuring flask and filled up to the mark with the solvent (corresponds to a dilution of 1:250=4000 $\mu$g/ml). The further dilution series was standardized with distilled water or the respective solvent and the following substance concentrations were prepared: 1000; 250; 62.5 $\mu$g/ml.

Execution of the test

The tubes were filled with 4.9 ml of the corresponding liquid nutrient medium. Then 0.1 ml of the substance dilution prepared above was added to each tube, so that the mentioned final concentrations were present. Finally each tube was inoculated with 0.1 ml of the standardized suspension of microorganisms. Control tests merely using the solvent are to be carried out simultaneously.

Incubation

Bacteria were incubated at 37° C. for 18–20 hours and fungi at 27° C. for 7 days.

Evaluation

The measurement is carried out macroscopically defining the minimal inhibitory concentration (the lowest still microbiostatically effective concentration).
Agar diffusion test:

Nutrient media

1. Meat extract agar: for St. aureus SG 511

| Recipe: | Peptone | 10 gm |
|---|---|---|
| | Meat extract | 8 gm |
| | Sodium chloride | 3 gm |
| | Sec. sodium phosphate (Na$_2$HPO$_4$) | 2 gm |
| | Pronagar | 15 gm |
| | ad 1,000 ml of distilled water | (pH 7.2–7.4) |

Sterilization: 15 min. at 120° C. in the autoclave

2. Glucose agar: for Sc. Aronson and St. pyogenes
Recipe see meat extract agar. After sterilization 1 weight percent of glucose is added as a sterile 50% solution.

3. Sabouraud agar: for C. alb., Trich. ment., A. niger

| Recipe: | Peptone from Casein | 10 gm |
|---|---|---|
| | Glucose | 40 gm |
| | Sodium chloride | 1 gm |
| | Sec. sodium phosphate (Na$_2$HPO$_4$) | 1 gm |
| | Pronagar | 15 gm |
| | ad 1,000 ml of distilled water | |

Sterilization: 5–10 min. at 120° C., a pH was not adjusted.

Standardization of the density of microorganisms

The age of the primary cultures is 24 hours for bacteria and 14 days for fungi. The standardization of the suspension of microorganisms is effected using a photometer according to Eppendorf (test tube φ14 mm, filter 546 nm) and a suspension for comparison consisting of barium sulfate, this suspension being created by addition of 3.0 ml of 1% barium chloride solution to 97 ml of 1% sulfuric acid. After the standardization St. aureus SG 511 was diluted 1:1000 and Sc. pyogenes and Aronson 1:100 by means of sodium chloride solution. The fungi were used in an undiluted state.

Preparation of the substance concentration 40 mgm of the substance were put into a 10 ml measuring flask and filled up to the mark with the solvent (corresponds to a dilution of 1:250=4000 μg/ml). The dilutions to the concentrations under test were effected with distilled water or the respective solvent.

Execution of the test 19 ml of the nutrient medium were filled into sterile Petri dishes of a diameter of 8 cm and dried. Subsequently the agar plates were charged with 4 ml of seed agar. 100 ml of seed agar contain 1.25 ml of the suspension of microorganisms, an agar plate thus containing 0.05 ml of the suspension of microorganisms. After solidification of the agar, 5 holes of a diameter of 5 mm were punched into the plates and filled with 0.05 ml of the correspondingly concentrated substance solution.

Control tests merely using the solvent are to be carried out simultaneously.

Incubation

Bacteria were incubated at 37° C. for 18–20 hours and fungi at 27° C. for 7 days.

Evaluation

The diameter of the area of inhibition in mm was measured after having deducted the diameter of the hole. If instead of a growth free zone only considerably reduced growth has taken place, these values were put into brackets.

Serial dilution test for Corynebacterium acnes and Pityrosporum ovale Nutrient medium For Corynebacterium acnes: thioglycolate-broth for Pityrosporum ovale: Littmann's broth, 5 ml per tube.

Density of microorganisms

Suspension of microorganisms in 0.9% sodium chloride solution, standardized using a photometer according to Eppendorf by means of a suspension for comparison consisting of barium sulfate, for Corynebacterium acnes in a dilution of 1:100, for Pityrosporum ovale in an undiluted state. 0.1 ml of the suspensions was used per test tube. Dimethyl sulfoxide served as a solvent for the substances.

The suspension with Corynebacteria acnes was incubated at 37° C. for 48 hours, the suspension of Pityrosporum ovale at 27° C. for 7 days. The reading was effected by macroscopic evaluation of the growth of microorganisms and registration of the minimal inhibitory concentration.

Agar diffusion test for Pityrosporum ovale CBS 1878 Nutrient medium

Littmann's agar, 23 ml per Petri dish, diameter of dish 100 mm.

Density of microorganisms

Suspension of microorganisms in 0.9% sodium chloride solution, standardized using a photometer according to Eppendorf by means of a suspension for comparison consisting of barium sulfate. 0.05 ml per plate were used. The test substances were dissolved in dimethyl sulfoxide. The incubation time was 7 days at 27° C.; the area of inhibition in mm was measured, 0.05 ml of the solution of the substance were used for each punch-hole of a diameter of 6 mm. The results of these tests are recorded in the following tables 1 and 2:

TABLE I

| | Activity on grampositive bacteria and Corynebacterium acnes: MIC-values in μg/ml | | | | | | |
|---|---|---|---|---|---|---|---|
| | Staphylococcus aureus SG 511 | | Streptococcus Aronson | | Streptococcus pyogenes | | Corynebacterium acnes |
| Substance | A.D.T. | S.D.T. | A.D.T. | S.D.T. | A.D.T. | S.D.T. | S.D.T. |
| A | 1000 | 80 | 1000 | 80 | nt | nt | 80 |
| B | 250 | 20 | 250 | 20 | 250 | 20 | 20 |
| C | 62.5 | 5 | 62.5 | 5 | 62.5 | 1.25 | 1.25 |
| D | >4000 | >80 | >4000 | >80 | >4000 | >80 | >80 |
| E | ≦15.6 | 1.25 | ≦15.6 | 0.31 | ≦15.6 | 0.31 | 0.08 |
| F | 62.5 | 0.08 | ≦15.6 | 1.25 | ≦15.6 | 1.25 | 0.31 |
| G | ≦15.6 | 0.31 | ≦15.6 | 1.25 | ≦15.6 | 0.31 | 1.25 |
| H | ≦15.6 | 0.31 | ≦15.6 | 1.25 | ≦15.6 | 0.31 | 1.25 |
| I | ≦15.6 | 0.31 | ≦15.6 | 0.08 | ≦15.6 | 0.31 | 0.08 |
| J | ≦15.6 | 5(1.25) | ≦15.6 | 5 | ≦15.6 | 1.25(0.08) | 0.02 |
| K | ≦15.6 | 1.25 | ≦15.6 | 1.25 | ≦15.6 | 0.31 | 0.08 |
| L | 62.5 | 0.31 | ≦15.6 | 0.31 | 62.5 | 0.08 | 1.25(0.31) |
| M | 250 | 1.25 | ≦15.6 | 20(1.25) | ≦15.6 | 1.25 | 0.31 |
| N | ≦15.6 | 1.25 | ≦15.6 | 1.25 | 62.5 | 0.31 | 0.31 |
| O | ≦15.6 | 0.31 | ≦15.6 | 0.31 | ≦15.6 | 0.08 | 1.25(0.31) |

TABLE I-continued

| | Activity on grampositive bacteria and Corynebacterium acnes: MIC-values in μg/ml | | | | | | |
|---|---|---|---|---|---|---|---|
| | Staphylococcus aureus SG 511 | | Streptococcus Aronson | | Streptococcus pyogenes | | Corynebacterium acnes |
| Substance | A.D.T. | S.D.T. | A.D.T. | S.D.T. | A.D.T. | S.D.T. | S.D.T. |
| P | 62.5 | 1.25 | ≦15.6 | 1.25 | 62.5 | 1.25 | 5(1.25) |
| Q | ≦15.6 | 0.08 | ≦15.6 | 1.25 | ≦15.6 | 0.001 | 0.02 |
| R | ≦15.6 | 0.08 | ≦15.6 | 0.31 | ≦15.6 | 0.005 | 0.005 |
| S | ≦15.6 | 1.25 | ≦15.6 | 1.25 | ≦15.6 | 1.25 | 0.31 |

Values in brackets mean that reduced growth has taken place at this concentration; nt=not tested; MIC=minimal inhibitory concentration; A.D.T.=agar diffusion test; S.D.T.=serial dilution test

TABLE II

| | Activity on yeasts, dermatophytes, molds and Pityrosporum ovale: MIC-values in μg/ml | | | | | | | |
|---|---|---|---|---|---|---|---|---|
| | Candida albicans | | Trichophyton mentagrophytes | | Aspergillus niger | | Pityrosporum ovale | |
| Substance | A.D.T. | S.D.T. | A.D.T. | S.D.T. | A.D.T. | S.D.T. | A.D.T. | S.D.T. |
| A | 1000 | 80 | 250 | 20 | 250 | 20 | 1000 | 80 |
| B | 1000 | 20 | 250 | 5 | 250 | 20 | 1000 | 80 |
| C | 1000 | 20 | 62.5 | 1.25 | 1000 | 5 | 1000 | >80 |
| D | >4000 | >80 | >4000 | >80 | >4000 | >80 | >4000 | >80 |
| U | 1000 | 20 | 250 | 5 | 250 | 20 | 1000 | 10 |
| V | 4000 | 80 | 250 | 20 | >4000 | >80 | 4000 | 20 |
| F | 250 | 20 | ≦15.6 | 1.25 | 250 | 20 | 250 | 80 |
| H | 1000 | (80) | ≦15.6 | 1.25 | 62.5 | (80) | 1000 | >80 |
| W | 1000 | (20) | ≦15.6 | 1.25 | 250 | 5 | 250 | 80 |

Measurement of the inhibition of the glucose-6-phosphatedehydrogenase

The equilibrium was observed:

Glucose-6-phosphate+NADP$^+$ ⇌ G6-DH gluconic acid-6-phosphate+NADPH+H$^+$ (NADP=nicotinamide-adenine-dinycleotide-phosphate, G6P-DH=gluconic acid-6-phosphate-dehydrogenase)

The formation velocity of NADPH is a measure for the enzyme activity; it may be observed by means of the extinction increase at 340, 334 or 366 nm per unit of time.

Method 0.025 ml of glucose-6-phosphate-dehydrogenase (Boehringer Mannheim) were filled up to 10 ml of distilled water (solution I). 100 mgm of nicotinamide-adeninedinucleotide-phosphate were dissolved in 13 ml of distilled water (solution II). 47.2 mgm of glucose-6-phosphate were dissolved in further 10 ml of distilled water (solution 3). Simultaneously a buffer solution (solution IV) was prepared as follows: 0.28 gm of triethanolamine-hydrochloride and 1.461 gm of ethylene diaminotetraacetic acid-disodium salt were dissolved in 1 liter of distilled water and adjusted to a pH of 7.6 with sodium hydroxide solution. The substance under test was dissolved in dimethyl formamide or ethanol (solution V). Tested concentrations: 50; 25; 12.5; 6.25; 3.125; 1.56 and 0.78 μg/ml.

Determination of the immediate inhibition 0.1 ml of solution I, 0.1 ml of solution II, 2.67 ml of solution IV and 0.03 ml of solution V were mixed and kept at 25° C. for 5 minutes. Then 0.1 ml of solution III was added, mixed and the alteration of extinction was determined spectrophotometrically at 366 nm for 3 minutes.

Determination of the inhibition of incubation 0.1 ml of solution I, 0.1 ml of solution II, 2.67 ml of solution IV and 0.03 ml of solution V were mixed and kept at 37° C. for 60 minutes. Then 0.1 ml of solution III was added, mixed and the alteration of extinction was measured spectrophotometrically at 366 nm for 3 minutes.

The inhibitory values were calculated from the average values of three measurements (alteration of extinction per minute) compared with controls, which received the pure solvent as the inhibitory solution. Then the ED$_{50}$ was calculated according to Reed and Muench from the inhibitory values for the various concentrations.

The following table contains the results:

TABLE III

| | G6PDH-inhibition | |
|---|---|---|
| | Ed$_{50}$ [μg/ml] | |
| Substance | Immediate Inhibition | Inhibition of Incubation |
| A | >50 | 33 |
| B | 34.5 | 30 |
| C | 37.5 | 20 |
| D | >50 | >50 |
| E | 24.1 | 22.3 |
| F | 37.7 | 27.7 |
| J | 8.5 | 3.62 |
| L | 4.0 | 3.25 |
| M | 2.8 | 2.9 |
| N | 10.6 | 6.5 |
| O | 10.2 | 6.9 |
| P | 14.8 | 9.9 |
| Z | 0.58 | 0.13 |

Measurement of the inhibition of cell cultures

Method

HeLa-cell culture was treated with trypsin and adjusted to a cell number of 150,000 cells/ml of fresh medium. The substance was always dissolved in the same quantity of dimethyl sulfoxide and then further diluted with growth medium. 0.1 ml of the substance-dilutions were added to each well of microtiter plates and then 0.2 ml of cell suspension were added (4 wells per dilution). Several growth controls containing 0.1 ml of growth medium instead of 0.1 ml of substance dilution were put up. After careful mixing, the cultures were incubated at 37° C. for 3 days in a 5% carbon dioxide atmosphere. The reading was effected in comparison with these controls. The results were given as the percentage of the deficiency and degeneration compared to the growth control. The minimal inhibitory concentration was determined from these results and the $ED_{50}$ was calculated according to Reed and Muench. The statements are referred to µg of substance per ml of total medium.

The results are recorded in the following table:

TABLE IV

| Substance | Minimal inhibitory concentration µg/ml | $ED_{50}$ µg/ml |
|---|---|---|
| A | 3.13 | 12.5 |
| B | 6.25 | 9.75 |
| D | 25 | 90.1 |
| E | 0.78 | 5.81 |
| V | ≦0.78 | 1.5 |
| F | 0.78 | 7.7 |
| G | 0.78 | 5.8 |
| H | ≦0.78 | 4.2 |
| K | 0.78 | 2.27 |
| N | 3.13 | 5.32 |
| P | 1.56 | 3.52 |
| S | ≦0.78 | 3.8 |

The compounds of this invention are chemically stable, show a good lipophilic behavior (distribution-coefficient n-octanol/water > 1000) and may well be incorporated into ointments, creams, tinctures, sprays, powders etc., which are suitable for topical application.

The good compatibility on the skin (a cream containing 10% of compound E was tolerated without irritation for over 24 hours under occlusion) and the low toxicity are of special advantage.

The acute toxicity was determined with mice. The $LD_{50}$, the dose leading to the death of 50% of the animals within 14 days, was calculated. $LD_{50}$ in the mouse:

| Compound E | p.o. | >3,200 mgm/kg |
| | s.c. | >4,000 mgm/kg |
| | i.p. | 82 mgm/kg |
| Compound Q | p.o. | >4,000 mgm/kg |
| | s.c. | >2,0000 mgm/kg |
| | i.p. | 400 mgm/kg |

In the general pharmacologic screening of the substances, which indicates an influence on essential body functions, e.g. heart/circulation or central nervous system, no considerable effects were shown. Systemic side-effects are, therefore, not expected with local application.

Because of the good lipophilic behavior at simultaneous presence of polar groups the compounds penetrate well into the skin, however, they are only absorbed to a small extent as could be shown by analysis of the excretion.

The examination on the compatibility on the skin and sensitization, which were carried out with guinea pigs, showed that the weak sensitizing properties of some resorcinols disappear by the introduction of the trifluoroacetyl group. As resorcinols, such as hexyl-resorcinol, in some cases cause allergies in humans, this is a considerable advantage.

At present an effective therapy of acne is only possible systemically with strong antibiotics (tetracycline, erythromycin) and locally with peeling agents such as vitamin-A-acid and benzoyl peroxide. The application of antibiotics for a disease by no means endangering life is problematic in principle because of the resistance formation, when peeling agents are applied one must expect considerable irritation of the skin.

In the acne-therapy with antibiotics the gram-positive bacteria important for acne, above all Corynebacterium acnes, are dimished, which leads to a reduction of the content of free fatty acids, which were split off from triglycerides by these bacteria, in the sebum.

As table I shows, the above-mentioned compounds are strongly active against Corynebacterium acnes. In addition, it could be shown that after local application a considerable reduction of the content of free fatty acids is possible. Thus, a local therapy is possible, which may be compared in its effect with the oral therapy with antibiotics.

The exact cause of dandruff formation is unknown up to now. However, a hyperkeratosis may be found with dandruff, i.e. mitosis in the epidermis is accelerated; additionally the hyperkeratosis is disturbed. According to the statements of some authors, e.g. R. A. Gosse, R. W. VanderWyck, J. Soc. Cosmet. Chem. 20, 603 (1969), the yeast Pityrosporum ovale plays a role for the genesis of dandruff.

Table II shows that some of the above-mentioned compounds have a strong effect against Pityrosporum ovale.

It may be seen in Tables III and IV that these and other compounds can delay accelerated mitosis processes. Thus, a therapy of dandruff is possible with compounds showing a good activity in Tables II, III and IV.

At present an effective therapy of psoriasis is only possible topically with dithranol, tar preparations and highly active corticoïdes and systemically with antimetabolites such as methothrexate, corticosteroids and cytostatics. Additionally, the physical treatment with UV-light, X-rays and the combined application of psoralens (systemically and locally) and UV-light are used. All these treatment methods are either circumstantial or accompanied by considerable side-effects. Therefore, a simple effective local therapy is of advantage. Tables III and IV show that some of the abovementioned compounds may be used for psoriasis-therapy.

Mycoses of the skin are becoming more frequent. As the kind of microorganism causing an irritation often cannot be determined, the application of broad spectrum antimycotics against dermatophytes, yeasts and bacteria is of special advantage.

Tables I and II show that the above-mentioned compounds are strongly active against these microorganisms and may, therefore, be used for therapy of mycoses and bacterial skin infections.

The compounds of the formula I may be incorporated into the usual pharmaceutical preparations, such as foam aerosols, powder-sprays, powders, throat sprays, shampoos, creams, ointments, tinctures, pastes or gels. The dosage of the active ingredients is between 0.05 and 1% by weight, preferably 0.1 to 0.8 percent by weight.

EXAMPLE I

Foam aerosol (filling/can: 60 gm) containing 0.5% by weight of
2,4-dihydroxy-5-n-hexyl-trifluoroacetophenone
(quickly breaking foam)

| | |
|---|---|
| Active ingredient | 0.30 gm |
| Cremophor EL = reaction product of castor oil with ethylene oxide (1 mol:40 mol) | 0.50 gm |
| Tween 80 = polyethoxylated sorbitanmono-oleate | 0.80 gm |
| Texapon N 25 = sodium laurylether sulfate | 0.50 gm |
| French brandy essence | 0.25 gm |
| Ethanol 96% | 12.75 gm |
| Water | 35.00 gm |
| Propellant mixture ad | 60.00 gm |
| (Frigen 12/114 in the proportion of 60:40 parts by volume) | |

(a) Solution of active ingredient

The active ingredient, Cremophor EL and the French brandy essence were successively dissolved in ethanol at room temperature.

Tween 80 and Texapon N 25 were dissolved in water, also at room temperature, combined with the ethanolic solution and filtered.

(b) Preparation of aerosol 50.1 gm of the solution of active ingredient were filled into an alu-monobloc can of suitable size provided in the inside with a double protecting coat of lacquer. The can closed with a valve was subsequently filled with 9.9 gm of propellant mixture by means of a propellant filling equipment.

EXAMPLE II

Powder spray (filling/can: 100 gm) containing 0.5% by weight of
2,4-dihydroxy-5-n-hexyl-trifluoroacetophenone

| | |
|---|---|
| Active ingredient | 0.50 gm |
| Aerosil (colloidal silicic acid) | 0.50 gm |
| ANM-maize (corn starch) | 2.00 gm |
| Isopropyl myristate | 0.50 gm |
| Propellant mixture ad | |
| (Frigen 11/12 in the proportion of 50:50 parts by volume) | |

(a) Powder of active ingredient

The active ingredient was ground in a pinned disk mill together with the aerosil and the corn starch and triturated with the isopropyl myristate in a mortar.

(b) Preparation of aerosol 3.5 gm of the powder of active ingredient were filled into an alu-monobloc can of suitable size. The can closed with a valve was subsequently filled with 96.5 gm of propellant mixture by means of a propellant filling equipment.

EXAMPLE III

Powder containing 0.5% by weight of
2,4-dihydroxy-5-n-hexyl-trifluoroacetophenone

| | |
|---|---|
| Active ingredient | 0.50 gm |
| Aerosil 200 | 0.50 gm |
| Magnesium stearate | 0.20 gm |
| Lactose | 48.80 gm |
| ANM-maize (corn starch) | 50.00 gm |

The micronized active ingredient was mixed with Aerosil 200, magnesium stearate, lactose and corn starch and subsequently ground in a pinned disk mill.

EXAMPLE IV

Throat spray containing 0.5% by weight of
2,4-dihydroxy-5-n-hexyl-trifluoroacetophenone

| | |
|---|---|
| Active ingredient | 0.50 gm |
| Glycerin | 20.00 gm |
| Sodium saccharin | 0.02 gm |
| Ethanol 96% | 10.00 gm |
| Cremophor RH 40 = reaction product of hydrogenated castor oil with ethylene oxide | 1.00 gm |
| Menthol 42°–44° C. | 0.05 gm |
| Flavoring | 0.04 gm |
| Dyestuff blue | q.s. |
| Distilled water ad | 100.00 gm |

The active ingredient was dissolved in ethanol together with menthol and aroma and subsequently glycerin was added. In a portion of the water Cremophor RH 40, sodium saccharin and dyestuff were dissolved successively, this solution was combined with the ethanol-glycerin solution, filled up with water and filtered. Spraying is effected by means of a mechanical pump metering valve.

EXAMPLE V

Shampoo containing 0.1% by weight of
2,4-dihydroxy-5-n-hexyl-trifluoroacetophenone

| | |
|---|---|
| Active ingredient | 0.10 gm |
| Comperlan KD = coconut fat acid diethanol-amide | 3.00 gm |
| Zetesol 856 T = fatty alcohol ether sulfate | 25.00 gm |
| Lamepon S-TR = condensation product of protein hydrolyzates with vegetable fatty acids | 5.00 gm |
| Euperlan PK 771 = fatty alcohol ether sulfates | 10.00 gm |
| Cetiol HE = polyol fatty acid esters | 2.50 gm |
| Chemoderm = perfume oil composition | 0.50 gm |
| Dyestuff (yellowish orange 11963) | 0.012 gm |
| Nip-Nip (8/2) = methyl p-hydroxybenzoate + n-propyl p-hydroxy-benzoate | 0.20 gm |
| Distilled water ad | 100.00 gm |

Nipagine/Nipasol (Nip/Nip) were dissolved in a portion of the water while heating; subsequently Comperlan, Zetesol 856 T, Lamepon S-TR, Euperlan, Cetiol HE and dyestuff were successively stirred in at room temperature.

After addition of the active ingredient and homogenizing well the perfume was added.

EXAMPLE VI

Gel containing 0.5% by weight of
2,4-dihydroxy-5-n-hexyl-trifluoroacetophenone

| Active ingredient | 0.50 gm |
|---|---|
| Tween 80 = polyethoxylated sorbitan-mono-oleate | 0.10 gm |
| Carbopol 940 = acrylic acid polymerizate | 0.75 gm |
| Nip-Nip (8/2) | 0.30 gm |
| Silicone oil AK 350 | 3.00 gm |
| Triethanolamine solution 10% | 3.70 gm |
| Water ad | 100.00 gm |

Nipagine and Nipasol were dissolved in a portion of the water while heating, and Carbopol was added at about 50° C. while stirring vigorously.

The micronized active ingredient was suspended in the remaining water, mixed with Tween and added to the Carbopol suspension. Subsequently the silicone oil was stirred in, and the viscosity was adjusted while further stirring with triethanolamine.

EXAMPLE VII

Cream containing 0.8% by weight of
2,4-dihydroxy-5-n-hexyl-trifluoroacetophenone

| Active ingredient | 0.8 gm |
|---|---|
| Isopropyl myristate | 7.0 gm |
| Silicone oil AK 350 | 0.5 gm |
| Tween 60 | 2.0 gm |
| Span 60 | 2.0 gm |
| Lanette 0 | 7.0 gm |
| Propylene glycol 1.2 | 7.0 gm |
| Nip-Nip (8/2) | 0.3 gm |
| Distilled water | 73.4 gm |

Isopropyl myristate, silicone oil, Tween, Span and Lanette were melted at 75° C. and kept at this temperature. Propylene glycol, Nip/Nip (8/2) and water were boiled for a short time and cooled to 75° C. The active ingredient was stirred into the isopropyl myristate melt; this mixture was stirred into the propylene glycol mixture, the finished mixture was allowed to cool.

For use in plant protection the compounds according to the invention are processed into conventional formulations, especially into solution- or emulsion-concentrates, dusts, granulates, spray powders, seed-treatment powders and -solutions. The content of active substance in the sprays and dusts amounts from 0.01 to about 3% by weight. The seed-treatment solutions (about 10 to 50% by weight) and seed-treatment powders (about 20 to 90% by weight) as well as the concentrates (up to about 95% by weight) comprise higher concentrations of active substance.

Examples for formulation:
1. Suspension Powder:
   30 parts by weight of 2,4-dihydroxy-3-methyl-5-chloro-trifluoroacetophenone
   9 parts by weight of sodium lignin sulfonate
   1 part by weight of sodium naphthalene sulfonate
   60 parts by weight of colloidal silicic acid The components are ground homogeneously. For use as herbicide there is produced an aqueous spray with a content of active ingredient of 0.01 to 3% by weight. The spray may be used for the control of undesired monocotyledons, such as wild oats, as well as weeds (dicotyledons) in cereal and other cultures. When applying higher doses, the use as total herbicide is possible too.

The other compounds of the formula I may be used in a corresponding way.

2. Seed-treatment Solution:
   20 parts by weight of 2,4-dihydroxy-5-tert.butyl-trifluoroacetophenone 79 parts by weight of dimethyl formamide
3. Seed-treatment Powder:
   80 parts by weight of 2,4-dihydroxy-5-tert.butyl-trifluoroacetophenone
   3 parts by weight of magnesium stearate
   17 parts by weight of talcum The agents for seed-treatment are sprayed on (solution) or admixed with the seeds (powder). They serve for the control, above all, of the genera of fungi tiletia, helmintosporium, ustilago and fusarium.

The other compounds of the formula I may be used in a corresponding manner.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

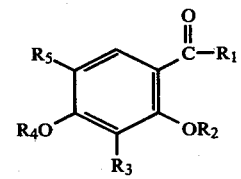

wherein
$R_1$ is perfluoralkyl of 1 to 8 carbon atoms,
$R_2$ and $R_4$ are each hydrogen or alkyl of 1 to 10 carbon atoms,
$R_3$ is methyl, alkyl of 3 to 18 carbon atoms, halogen, nitro, methylthio, hydroxyl or methoxy,
$R_5$ is methyl, alkyl of 3 to 18 carbon atoms, halogen, nitro or methylthio, or
one of the substituents $R_3$ and $R_5$ is hydrogen or ethyl when the other has the meanings defined above except hydrogen, or when $R_1$ has the meanings defined above except trifluoromethyl, or when $R_2$ and $R_4$ have the meanings defined above except hydrogen or methyl.

2. The compound of claim 1, which is 2,4-dihydroxy-5-n-hexyl-trifluoroacetophenone.

3. The compound of claim 1, which is 2,4-dihydroxy-5-iso-pentyl-trifluoroacetophenone.

4. The compound of claim 1, which is 2,4-dihydroxy-5-n-nonyl-trifluoroacetophenone.

5. The compound of claim 1, which is 2,4-dihydroxy-3-iso-hexyl-trifluoroacetophenone.

6. The compound of claim 1, which is 2,4-dihydroxy-3-methyl-trifluoroacetophenone.

7. The compound of claim 1, which is 2,4-dihydroxy-3-isopropyl-trifluoroacetophenone.

8. The compound of claim 1, which is 2,4-dihydroxy-3-iso-butyl-trifluoroacetophenone.

9. The compound of claim 1, which is 2,4-dihydroxy-5-n-decyl-trifluoroacetophenone.

10. The compound of claim 1, which is 2,4-dihydroxy-3-isodecyl-trifluoroacetophenone.

11. The compound of claim 1, which is 2,4-dihydroxy-3-methyl-pentafluoropropiophenone.

12. An antibacterial and antifungal pharmaceutical composition consisting essentially of an inert carrier and from 0.05 to 1% by weight, based on the total weight, of a compound of claim 1.

13. The method of inhibiting the growth of bacteria and fungi which comprises contacting said bacteria and fungi with a composition of claim 19.

14. The compound of claim 1, which is 2,4-dihydroxy-3-methyl-5-chloro-trifluoroacetophenone.

15. The compound of claim 1, which is 2,4-dihydroxy-5-tert.butyl-trifluoroacetophenone.

16. The compound of claim 1, which is 2,4-dihydroxy-3-isopropyl-5-chloro-trifluoroacetophenone.

* * * * *